United States Patent
Dalser et al.

(10) Patent No.: US 10,688,214 B2
(45) Date of Patent: Jun. 23, 2020

(54) VOLATILE SUBSTANCE EVAPORATION ELEMENT

(71) Applicant: ZOBELE HOLDING S.P.A., Trento (IT)

(72) Inventors: Alessio Dalser, Trento (IT); Andrea Pedrotti, Trento (IT); Stefano Deflorian, Trento (IT); Cedric Morhain, Barcelona (ES); Joaquim Llorente Alonso, Barcelona (ES)

(73) Assignee: ZOBELE HOLDING SPA (IT)

( * ) Notice: Subject to any disclaimer, the term of this patent is extended or adjusted under 35 U.S.C. 154(b) by 0 days.

(21) Appl. No.: 15/574,861

(22) PCT Filed: May 13, 2016

(86) PCT No.: PCT/EP2016/060852
§ 371 (c)(1),
(2) Date: Nov. 17, 2017

(87) PCT Pub. No.: WO2016/184809
PCT Pub. Date: Nov. 24, 2016

(65) Prior Publication Data
US 2018/0126026 A1      May 10, 2018

(30) Foreign Application Priority Data

May 18, 2015   (ES) .................................. 201530679

(51) Int. Cl.
*A61L 9/12*    (2006.01)
*A01M 1/20*    (2006.01)
*A61L 9/04*    (2006.01)

(52) U.S. Cl.
CPC ........... *A61L 9/127* (2013.01); *A01M 1/2055* (2013.01); *A61L 9/04* (2013.01); *A61L 9/12* (2013.01)

(58) Field of Classification Search
CPC .. A01L 9/04; A01L 9/12; A01L 9/121; A01M 1/2055; A61L 9/04; A61L 9/12; A61L 9/127
(Continued)

(56) References Cited

U.S. PATENT DOCUMENTS 1,897,573 A     2/1933  Curran
5,035,435 A *   7/1991  Burgeson .................. F42B 6/04
                                                 239/34

(Continued)

FOREIGN PATENT DOCUMENTS

EP     0 841 070 A2    5/1998
EP     2 832 375 A1    2/2015
(Continued)

OTHER PUBLICATIONS

International Search Report dated Jul. 13, 2016 in corresponding PCT International Application No. PCT/EP2016/060852.
(Continued)

*Primary Examiner* — Steven J Ganey
(74) *Attorney, Agent, or Firm* — Ostrolenk Faber LLP

(57) ABSTRACT

A volatile substance evaporation element including a rod impregnated with volatile substances, the rod being made of sintered wood. The porosity of the rod varies between its core and its surface, the porosity of said rod being lower on its surface than in its core, making it possible to increase the capacity of the core of the evaporation element to act as a receptacle for volatile substances.

14 Claims, 3 Drawing Sheets

(58) Field of Classification Search
USPC .................................... 239/34, 44, 53, 54
See application file for complete search history.

(56) References Cited

U.S. PATENT DOCUMENTS

| | | | |
|---|---|---|---|
| 5,422,078 A | 6/1995 | Colon | 422/123 |
| 6,071,529 A | 6/2000 | Ballard et al. | 424/408 |
| 2008/0087740 A1 | 4/2008 | Guesonoff et al. | 239/55 |
| 2012/0091221 A1* | 4/2012 | Levake | A61L 9/127 |
| | | | 239/44 |

FOREIGN PATENT DOCUMENTS

| | | |
|---|---|---|
| ES | 2 145 985 T3 | 7/2000 |
| GB | 2492370 A | 1/2013 |
| KR | 20-0469969 Y1 | 11/2013 |
| WO | WO 03/003826 A2 | 1/2003 |
| WO | WO 2006/002395 A2 | 1/2006 |
| WO | WO 2007/125384 A2 | 11/2007 |
| WO | WO 2011/121360 A1 | 10/2011 |

OTHER PUBLICATIONS

Written Opinion dated Jul. 13, 2016 in corresponding PCT International Application No. PCT/EP2016/060852.
Search Report dated Oct. 18, 2016 in corresponding Spanish Patent Application No. 201530679.
International Search Report dated Jul. 14, 2016 in corresponding PCT International Application No. PCT/EP2016/060847.
Written Opinion dated Jul. 14, 2016 in corresponding PCT International Application No. PCT/EP2016/060847.
Search Report dated Nov. 11, 2016 in corresponding Spanish Patent Application No. 201530677.

* cited by examiner

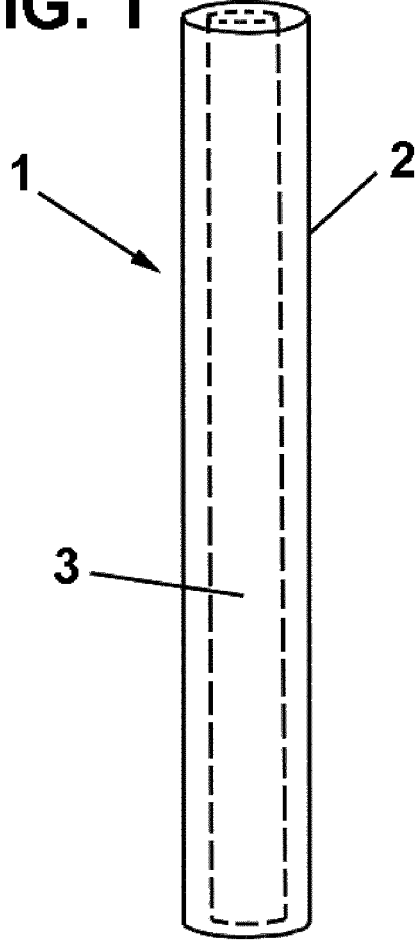

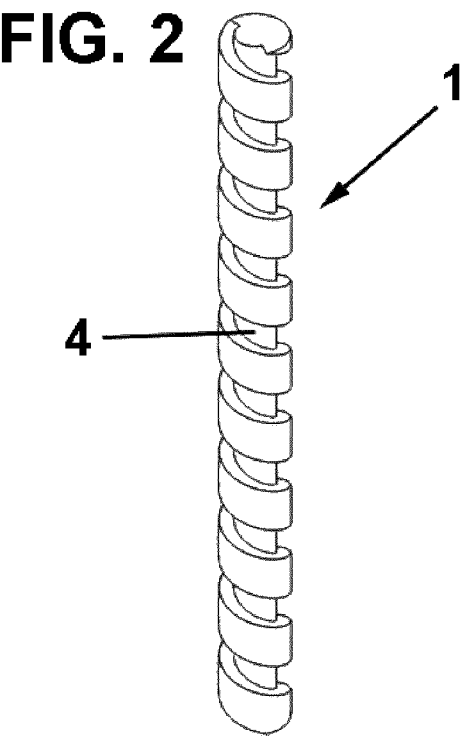
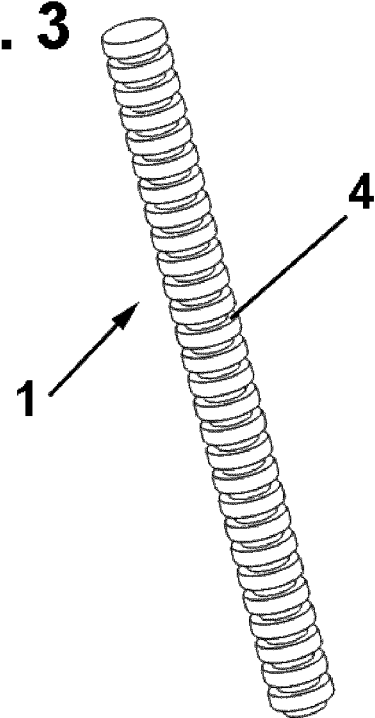
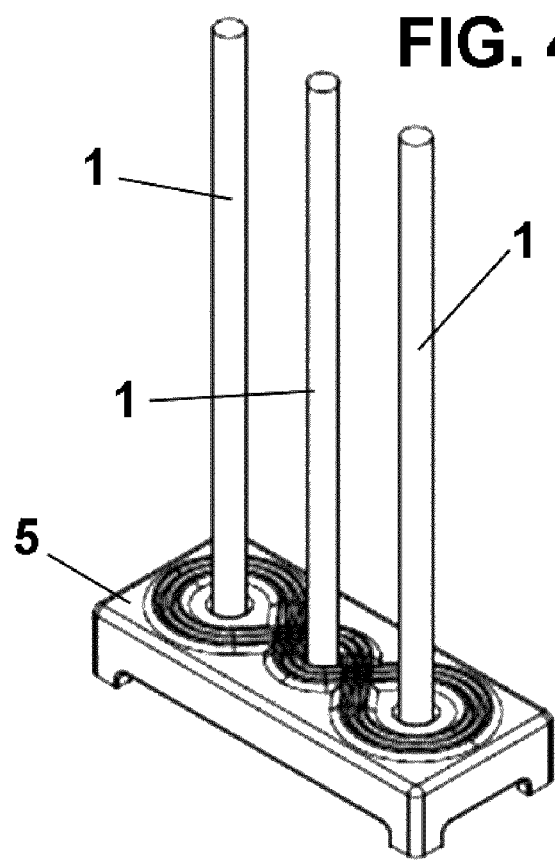

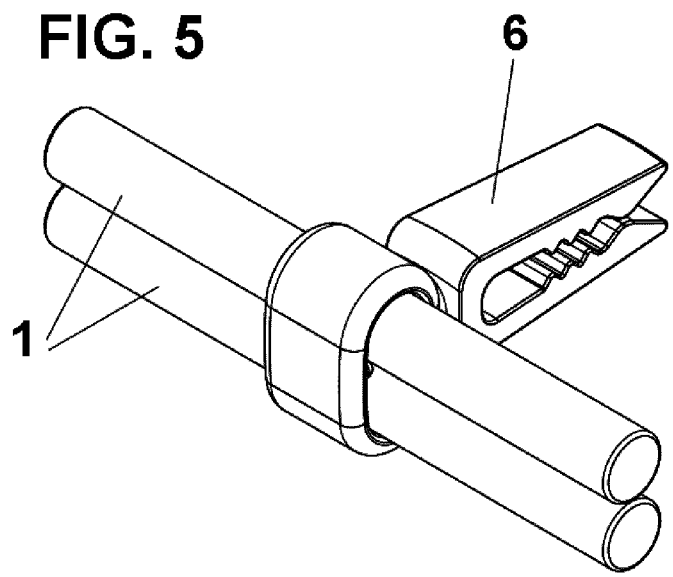

VOLATILE SUBSTANCE EVAPORATION ELEMENT

CROSS-REFERENCE TO RELATED APPLICATIONS

The present application is a 35 U.S.C. § 371 national phase conversion of PCT/EP2016/060852, filed May 13, 2016, which claims priority to Spanish Patent Application No. P201530679, filed May 18, 2015. The entire contents of both applications are incorporated in full herein by reference. The PCT International Application was published in the English language.

DESCRIPTION

The present invention relates to a volatile substance evaporation element that can be used as an air freshener or as insecticide.

BACKGROUND OF THE INVENTION

There are some very simple porous elements on the market that consist of a cylindrical rod made mainly of rolled paper impregnated with volatile substances. An example of these types of products is described in document WO2006/02395.

These very simple products are designed to be disposed on a support or hanged and to release the volatile substances under static conditions.

The use of these types of rolled and impregnated paper elements for evaporating volatile substances has various drawbacks.

On the one hand, the manner in which this paper is rolled makes the level of compaction higher in the centre than along the perimeter, reducing the capacity of the core to act as a receptacle for volatile substances.

On the other hand, its surface cannot be altered mechanically to increase the evaporation surface, since a cut in the external paper layer would cause the entire wrapping to break.

There is also the alternative of using wooden rods, but this type of material generally either has high porosity to contain volatile substances, but are mechanically weak or have a high level of density when they have poor absorption capacity but good mechanical resistance.

DESCRIPTION OF THE INVENTION

The volatile substance evaporation element of the invention makes it possible to resolve the aforementioned drawbacks and has other advantages that will be described below.

The volatile substance evaporation element in accordance with the present invention comprises a rod impregnated with volatile substances and is characterised in that said rod is made of sintered wood.

Advantageously, the porosity of said rod varies between its core and its surface. Preferably, the porosity of said rod is lower on its surface than in its core, for example, 10% lower, 30% lower or 50% lower on its surface than in its core.

According to a preferred embodiment, the length of the rod is at least seven times greater than the width of the rod and the rod is substantially cylindrical.

Advantageously, the core extends to up to 50% of the width of the rod or up to 70% of the width of the rod or up to 90% of the width of the rod.

Additionally, the rod may comprise at least one groove that extends along the length thereof, wherein said at least one groove may have a helical shape.

Preferably, the depth of said at least one groove is comprised between 50% and 10% of the width of the rod.

The volatile substance evaporation element in accordance with the present invention enables the obtainment of various advantages, such as:

It increases the capacity of the core of the evaporation element to act as a receptacle for volatile substances;

It enables the mechanical alteration of its surface to increase the evaporation surface, for example by making one or more grooves;

It enables the evaporation element to be sufficiently porous to adequately fulfil its evaporation function and, moreover, mechanically it is sufficiently resistant.

BRIEF DESCRIPTION OF THE DRAWINGS

In order to make the foregoing more readily understandable, a set of drawings is attached, wherein, schematically and by way of illustration and not limitation, an embodiment is represented.

FIG. 1 shows a perspective view of a volatile substance evaporation element in accordance with the present invention, indicating the core by means of dashed lines;

FIGS. 2 and 3 show perspective views of two embodiments of the volatile substance evaporation element in accordance with the present invention, which include grooves; and FIGS. 4 and 5 show perspective views of two possible uses of the volatile substance evaporation element in accordance with the present invention.

DESCRIPTION OF A PREFERRED EMBODIMENT

The volatile substance evaporation element of the present invention comprises a rod, preferably cylindrical, generally indicated by numerical reference 1. This rod 1 is made of sintered wood impregnated with volatile substances, i.e. made from the agglomeration of particles bonded together by means of a sintering process.

The sintering process consists of pouring a water-based paste with a wood-based paste and binding agents in a matrix and then letting the rod 1 dry to remove the water.

The sintering process enables the obtainment of a high level of compaction of the particles on the exterior portion of the rod 1, which will also cause the formation of a surface 2 with low porosity and a core 3 with high porosity.

The resulting rod 1 has a surface 2 and core 3 configuration, wherein the surface 2 has a lower porosity than that of the core 3. Naturally, it should be understood that reference is made to average porosity, since porosity varies throughout the width or radius of the rod 1.

The central core 3 with high porosity provides the rod 1 with a high capacity to absorb the volatile substances, whereas the surface 2 controls the release of the volatile substances, as well as its mechanical resistance.

Depending on the design and application, the distribution between the surface 2 and the core 3 can be established in different relationships.

Preferably, the width or radius of the core 3 is 70% of the width or radius of the rod 1. Alternatively, a value between 50% and 90% may be used.

In order to increase the evaporation surface, the external diameter of the rod 1 can be machined to form one or more grooves 4, for example, a helical groove, as can be observed in FIG. 2, and a plurality of transverse grooves, as can be observed in FIG. 3.

Preferably, the depth of this groove 4 must be sufficient to allow in the zone of the rod 1 referred to as surface 2, i.e. a depth comprised between 50% and 10% of the width of the rod 1.

As can be observed in FIGS. 4 and 5, the volatile substance evaporation element in accordance with the present invention can be used on its own or together with other elements on a support 5.

The rod 1 can be hanged, for example using a chain that passes directly through a possible hole made in the upper portion of the rod or fixed to a cover fixed to one end of the rod 1.

The rod 1 may also be fixed to a support 6 that can be coupled to the vent grille of a vehicle.

Although reference has been made to a specific embodiment of the invention, it is evident to the person skilled in the art that the volatile substance evaporation element described is susceptible of many variations and modifications, and that all the aforementioned details may be replaced with other, technically equivalent ones, without detracting from the scope of protection defined by the attached claims.

The invention claimed is:

1. A volatile substance evaporation element comprising:
a rod impregnated with volatile substances,
wherein said rod is made of sintered wood,
wherein the porosity of said rod varies between its core and its surface, and
wherein the core extends to up to between 50% and 90% of the width of the rod.

2. The volatile substance evaporation element according to claim 1, wherein the porosity of said rod is lower on its surface than in its core.

3. The volatile substance evaporation element according to claim 2, wherein the porosity of said rod is 10% lower on its surface than in its core.

4. The volatile substance evaporation element according to claim 2, wherein the porosity of said rod is 30% lower on its surface than in its core.

5. The volatile substance evaporation element according to claim 2, wherein the porosity of said rod is 50% lower on its surface than in its core.

6. The volatile substance evaporation element according to claim 1, wherein the length of the rod is at least seven times greater than the width of the rod.

7. The volatile substance evaporation element according to claim 1, wherein the rod is substantially cylindrical.

8. The volatile substance evaporation element according to claim 1, wherein the core extends to up to 50% of the width of the rod.

9. The volatile substance evaporation element according to claim 1, wherein the core extends to up to 70% of the width of the rod.

10. The volatile substance evaporation element according to claim 1, wherein the rod comprises at least one groove that extends along the length of the rod.

11. The volatile substance evaporation element according to claim 10, wherein said at least one groove has a helical shape.

12. The volatile substance evaporation element according to claim 10, wherein a depth of said at least one groove is between 50% and 10% of a width of the rod.

13. A volatile substance evaporation element comprising:
a rod impregnated with volatile substances,
wherein said rod is made of sintered wood, and
wherein the porosity of said rod varies between its core and its surface and is 10% lower on its surface than in its core.

14. A volatile substance evaporation element comprising:
a rod impregnated with volatile substances,
wherein said rod is made of sintered wood, and
wherein the porosity of said rod varies between its core and its surface and is 30% lower on its surface than in its core.

* * * * *